US011883953B2

(12) United States Patent
Ando et al.

(10) Patent No.: US 11,883,953 B2
(45) Date of Patent: Jan. 30, 2024

(54) PASSIVE JOINT DEVICE, CABLE GUIDE, AND POWER TRANSMISSION MECHANISM

(71) Applicant: A-Traction Inc., Kashiwa (JP)

(72) Inventors: Takehiro Ando, Kashiwa (JP); Keita Awano, Kashiwa (JP)

(73) Assignee: A-TRACTION INC., Kashiwa (JP)

( * ) Notice: Subject to any disclaimer, the term of this patent is extended or adjusted under 35 U.S.C. 154(b) by 447 days.

(21) Appl. No.: 17/104,664

(22) Filed: Nov. 25, 2020

(65) Prior Publication Data

US 2021/0170608 A1 Jun. 10, 2021

(30) Foreign Application Priority Data

Dec. 5, 2019 (JP) ................................ 2019-220499

(51) Int. Cl.
*B25J 17/00* (2006.01)
*B25J 17/02* (2006.01)
(Continued)

(52) U.S. Cl.
CPC ........... *B25J 17/0258* (2013.01); *B25J 9/102* (2013.01); *B25J 19/0029* (2013.01);
(Continued)

(58) Field of Classification Search
CPC .... B25J 17/0258; B25J 9/102; B25J 19/0029; F16H 25/00; F16H 25/122; F16H 19/04; F16H 37/02; F16H 25/12; F16H 25/125; A61B 34/71; A61B 34/30; A61B 2034/302; H02G 11/00
See application file for complete search history.

(56) References Cited

U.S. PATENT DOCUMENTS 4,771,979 A * 9/1988 Nakazawa ............. F16M 11/10
248/185.1

FOREIGN PATENT DOCUMENTS

EP 2597349 A2 5/2013
GB 2190703 A 11/1987
(Continued)

OTHER PUBLICATIONS

Decision to Grant a Patent dated Mar. 30, 2020, issued in counterpart JP Patent Application No. 2019-220499, w/ English machine translation (5 pages).

(Continued)

*Primary Examiner* — Randell J Krug
(74) *Attorney, Agent, or Firm* — Oliff PLC

(57) ABSTRACT

A passive joint device for supporting a rotation-side member rotatably about a horizontal axis in a vertical direction with respect to a fixed-side member, includes: a cylindrical cam member having a pair of cam surfaces symmetrically arranged about a horizontal axis, a pedestal slidably disposed along the horizontal axis fixed to the rotation-side member, the pedestal having a pair of cam followers that contact with each of the pair of cam surfaces, a spring disposed inside the horizontal axis and biasing the pedestal toward the fixed-side member along the horizontal axis, wherein the spring force causes the pair of cam followers to come into contact with the pair of cam surfaces, and provide upward rotational force to the rotation-side member to reduce the downward rotational force of the rotation-side member.

10 Claims, 7 Drawing Sheets

(51) Int. Cl.
*B25J 9/10* (2006.01)
*B25J 19/00* (2006.01)
*F16H 19/04* (2006.01)
*H02G 11/00* (2006.01)
*A61B 34/30* (2016.01)
*A61B 34/00* (2016.01)
*F16H 37/02* (2006.01)

(52) U.S. Cl.
CPC .............. *F16H 19/04* (2013.01); *H02G 11/00* (2013.01); *A61B 34/30* (2016.02); *A61B 34/71* (2016.02); *A61B 2034/302* (2016.02); *F16H 37/02* (2013.01)

(56) References Cited

FOREIGN PATENT DOCUMENTS

| JP | 2002-510137 A | 4/2002 |
| JP | 2004-520558 A | 7/2004 |
| JP | 2011-115906 A | 6/2011 |
| JP | 2018-175863 A | 11/2018 |
| WO | 02/065013 A1 | 8/2002 |

OTHER PUBLICATIONS

Extended European Search Report dated Feb. 10, 2021, issued in counterpart EP Application No. 20210847.8 (8 pages).

\* cited by examiner

PASSIVE JOINT DEVICE, CABLE GUIDE, AND POWER TRANSMISSION MECHANISM

BACKGROUND OF THE INVENTION

Field of the Invention

The present invention relates to a passive joint device for connecting arms in a medical robot or the like.

Description of the Related Art

Laparoscopic surgery is generally performed by a physician who performs incision, excision, and suture of an organ (hereinafter referred to as "surgeon"), by a physician who holds an endoscope (hereinafter referred to as "scopist"), and by a physician who pulls the organ or holds tension during incision in order to deploy the surgeon's visual field (hereinafter referred to as "assistant"). Some surgical support apparatus (also referred to as surgical support robots) used in laparoscopic surgery attempt to reduce the number of doctors required for surgery by controlling the posture of surgical tools such as forceps, endoscope, and electrocautery by one or more robot arms.

Surgical support apparatus used in conventional laparoscopic surgery can be roughly divided into those that perform actions of three persons, i.e., a surgeon, a scopist, and an assistant, and those that hold an endoscope with one arm. Console-type surgery support robots are known to serve as surgeon, scopist, and assistant, and a plurality of robot arms are disposed around a patient or above the patient.

As the mechanism of the robot arm, it can be roughly classified into two types: one in which the rotation center on the abdominal wall is mechanically determined, and the other in which the robot itself has a passive joint and it is supported with a degree of freedom with the abdominal wall as a fulcrum, as disclosed in Japanese Patent Laid-Open No. 2018-175863.

In a mechanism having a passive joint, there is a problem that the weight of the body on the distal side of the joint is applied to the abdominal wall. The weight on the abdominal wall may be compensated by a counterweight, but a very large mass is required for compactness, which is not practical. Therefore, as disclosed in Japanese Patent Laid-Open No. 2011-115906, a mechanism for compensating the self-weight by a spring has also been proposed, but in such a mechanism, the size of the joint portion becomes a problem.

When a passive joint is provided, power cannot be transmitted to the distal end side from the joint. Therefore, as disclosed in Japanese Patent Laid-Open 2018-175863, it was necessary to attach the actuator to the distal end side from the passive joint.

SUMMARY OF THE INVENTION

The present invention has been made in consideration of the above-mentioned problems, and has its object to enable a passive joint used in a medical robot or the like to reduce a downward direction force applied to an arm by a weight of a distal end side while suppressing enlargement of the joint.

According to a first aspect of the present invention, there is provided a passive joint device for supporting a rotation-side member rotatably about a horizontal axis in a vertical direction with respect to a fixed-side member, comprising: a cylindrical cam member having a cylindrical surface centered on the horizontal axis and fixed to the fixed-side member, the cam member having a pair of cam surfaces symmetrically arranged on the cylindrical surface about the horizontal axis and formed obliquely along the horizontal axis; a pedestal slidably disposed along the horizontal axis within the horizontal axis fixed to the rotation-side member, the pedestal having a pair of cam followers that contact with each of the pair of cam surfaces; a spring disposed inside the horizontal axis fixed to the rotation-side member, the spring biasing the pedestal toward the fixed-side member along the horizontal axis, wherein the spring force causes the pair of cam followers to come into contact with the pair of cam surfaces, push the pair of cam surfaces, and provide upward rotational force to the rotation-side member to reduce the downward rotational force of the rotation-side member by the weight applied to the rotation-side member.

According to a second aspect of the present invention, there is provided a cable guide for guiding a pair of cables one ends of which are fixed to a fixed-side member and the other ends of which are fixed to the rotation-side member, and used in a joint device in which a rotation-side member is rotatably supported about a rotation axis with respect to a fixed-side member, the cable guide comprising: a pipe-shaped member which is rotatably disposed with respect to the rotation axis; and a pair of portions whose envelope has a shape close to arc shape and which are formed to face each other on the outer surface of the pipe-shaped member, a pair of portions slidably guiding each of the pair of cables, wherein the cable guide rotates around the rotation axis while guiding the pair of cables as the pair of cables move in the same direction with each other by relative rotation between the fixed-side member and the rotation-side member.

According to a third aspect of the present invention, there is provided a power transmission mechanism used in a passive joint device in which a rotation-side member is rotatably supported about a rotation axis with respect to a fixed-side member and transmitting power from the fixed-side member to the rotation-side member, the power transmission mechanism comprising: a rotation driving source disposed on the fixed-side member; a rotation shaft coaxial with the rotation axis that is transmitted a rotational force from the rotation driving source; a worm gear disposed on the rotation shaft; a worm wheel engaging with the worm gear; and a rotation operation member fixed to the worm wheel, and rotating about an axis perpendicular to the rotation axis.

According to a fourth aspect of the present invention, there is provided a power transmission mechanism used in a passive joint device in which a rotation-side member is rotatably supported about a rotation axis with respect to a fixed-side member and transmitting power from the fixed-side member to the rotation-side member, the power transmission mechanism comprising: a rotation driving source disposed on the fixed-side member; a first rotation shaft coaxial with the rotation axis that is transmitted a rotational force from the rotation driving source; a second rotation shaft that is transmitted a rotational force from the first rotation shaft, a worm gear disposed on the second rotation shaft, a worm wheel engaging with the worm gear, a rotation operation member fixed to the worm wheel, and rotating about an axis perpendicular to the rotation axis.

DESCRIPTION OF THE EMBODIMENTS

Hereinafter, an embodiment in which the present invention is applied to a medical surgical support apparatus will be described in detail with reference to the accompanying drawings.

Figure 1:
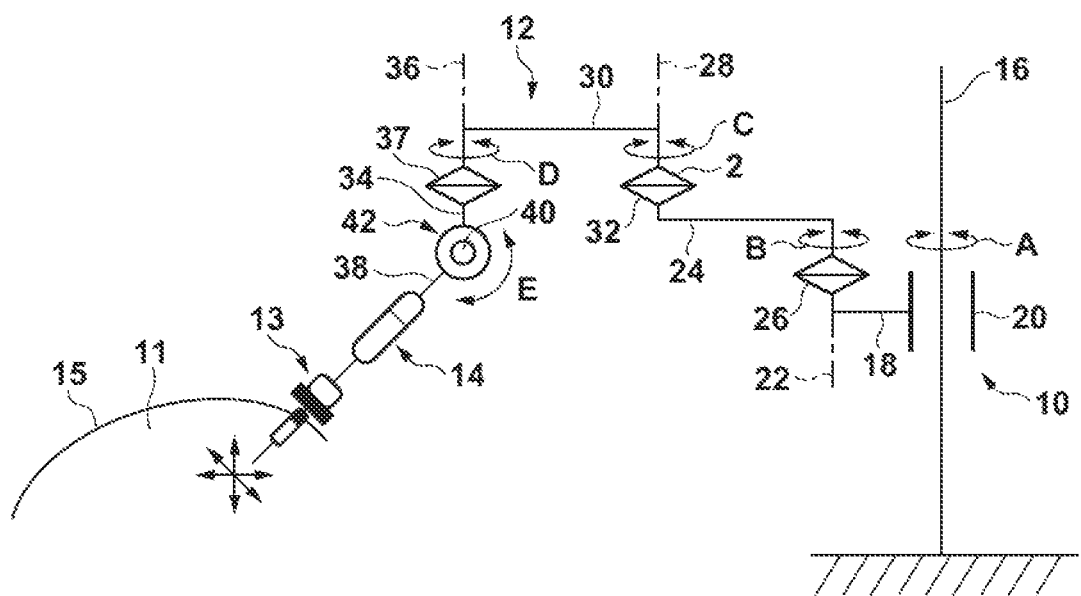
FIG. 1 is a diagram illustrating a configuration of a surgical support apparatus according to an embodiment of the present invention.

FIG. 1 is a diagram illustrating a configuration of a surgical support apparatus according to an embodiment of the present invention.

The surgical support apparatus 10 according to the present embodiment includes a robot arm 12 for controlling the posture of a surgical tool or an end effector inserted through a cannula 13 into a body cavity 11 of a patient. The surgical support apparatus 10 measures an insertion angle and an insertion depth of a surgical tool 14 that is inserted into the body cavity 11 by a surgeon and actually used for surgery (hereinafter, also referred to as a hand-carry medical tool). The robot arm 12 for controlling the posture of the surgical tool 14 or the end effector (hereinafter, also referred to as a robotic medical tool) is configured to be controlled in accordance with the measurement result.

More specifically, the robot arm 12 includes a first arm 18 which rotates around the rotation axis 16 in the vertical direction, an active joint 20 for actively rotating the first arm 18 in the direction of arrow A in the horizontal plane, a second arm 24 which rotates around the rotation axis 22 in the vertical direction of the tip of the first arm 18, and an active joint 26 for actively rotating the second arm 24 in the direction of arrow B in the horizontal plane. Further, robot arm 12 has a third arm 30 which rotates around the rotation axis 28 in the vertical direction of the tip of the second arm 24, and an active joint 32 for actively rotating the third arm 30 in the direction of arrow C in the horizontal plane.

On the distal end of the third arm 30, a first passive joint 37 for passively rotating the fixed-side member 34 in the direction of arrow D about the rotation axis 36 in the vertical direction is disposed. At the lower end of the fixed member 34, a second passive joint 42 is disposed which allows the rotation-side member 38 to be passively rotated about a horizontal axis (rotation axis) 40, which is a horizontal rotation axis, in the direction of arrow E (vertical direction).

That is, the robot arm 30 includes at least three-axis active joints 20, 26, and 32 having actuators, and first and second passive joints 37 and 42 having at least two axes, and holds the rod-shaped surgical tool 14 on the distal end side from the second passive joint 42. Generally, the axes of the first and second passive joints 37 and 42 are orthogonal to each other and intersect at one point, but the mechanism of the present embodiment can be realized even if the axes are not orthogonal to each other or do not intersect at one point.

The three-axis active joint may be any mechanism as long as the position and posture of the passive joint are uniquely determined, and is not limited to the configuration shown in FIG. 1. In each of the active joints 20, 26, 32 and the first and second passive joints 37, 42, an encoder for measuring the joint angle is disposed, and the position and orientation of the end effector can be uniquely determined by feeding back the position information.

Here, generally, in the configuration as shown in FIG. 1, there is a mass of the surgical tool 14 or the like at distal-side from the horizontal axis 40 of the second passive joint 42, by this mass, a downward force is applied to the abdominal wall 15. This places a burden on the patient. In order to prevent this, in the present embodiment, the second passive joint 42 is provided with the self-weight compensating mechanism 100.

Figure 2:
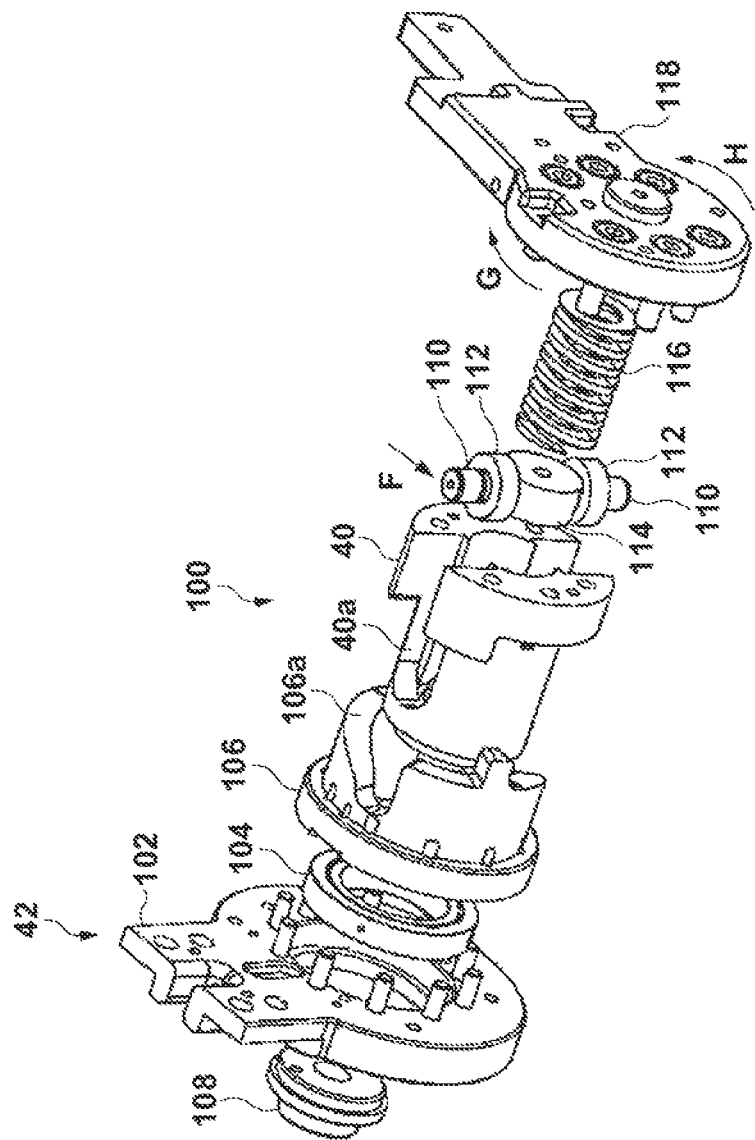
FIG. 2 is a diagram showing a configuration of a self-weight compensation mechanism according to an embodiment.

Hereinafter, the self-weight compensating mechanism 100 will be described. FIG. 2 is a diagram showing a configuration of the self-weight compensating mechanism 100 according to the present embodiment.

Self-weight compensating mechanism 100 disposed in the passive joint 42, as shown in FIG. 2, is mainly provided with a fixed-side member 102, a horizontal shaft bearing 104, a cylindrical cam member 106, a horizontal shaft 40, a horizontal shaft fixing member 108, a pair of cam followers 110, a pair of sliding bearings 112, a spring pedestal 114, a spring 116 and a rotation-side member 118. A pair of cylindrical cam surfaces 106a are formed on the cylindrical surface of the cylindrical cam member 106 so as to be symmetrical about the horizontal shaft 40. The cylindrical cam surfaces 106a in contact with the pair of cam followers are formed so as to be inclined along the direction of the horizontal shaft 40. The horizontal shaft 40 is fixed with respect to the rotation-side member 118, and is relatively rotatably supported with respect to the fixed-side member 102 by the horizontal bearing 104 and the horizontal shaft fixing member 108. Note that the cable guide described later is not included in this figure.

As shown in FIG. 2, a pair of cam followers 110, a pair of sliding bearings 112 are mounted symmetrically about the horizontal axis 40 on both sides of the spring pedestal 114, and biasing force of the spring 116 is applied to the spring pedestal 114 toward the fixed side member 102. Sliding bearing 112 is a bearing which is rotatable independently of the spring pedestal 114 and the cam follower 110, and rotates on the slide surface 40a of the horizontal shaft 40. That is, the cam followers 110, the spring pedestal 114, the slide bearings 112 follows the rotation of the horizontal shaft 40, receives a restraining force from the cylindrical cam surface 106a resisting the biasing force of the spring 116, and move along the horizontal shaft 40, and the rotation-side member 118 receives a force for rotating upward about the horizontal shaft 40. In other words, the rotation-side member 118 receives a rotational moment in the direction of the arrow G due to the weight of its tip, but the cam followers 110 contacting the cylindrical cam surface 106a receive a reaction force in the direction of the arrow F from the cylindrical cam surface 106a due to the biasing force of the spring 116. Therefore, on the rotation-side member 118, the rotational moment of the arrow H direction occurs, and the rotational moment due to the dead weight of the rotation-side member 118 is reduced, or canceled.

Here, in the present embodiment, since the cylindrical cam surfaces 106a are disposed symmetrically about the horizontal axis 40, the forces applied to the cam followers 110 are also symmetrical with respect to the axis, and a linear motion guide for accurately sliding the spring pedestal 114 is not necessary.

Figure 3:
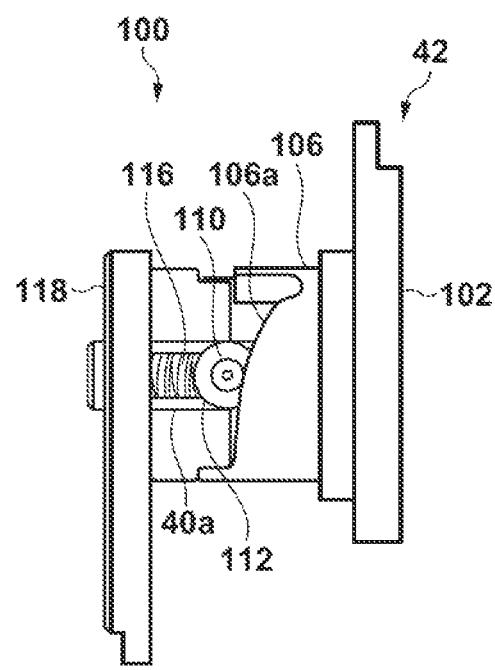
FIG. 3 is a view of a second passive joint viewed from the front.

FIG. 3 is a view of the second passive joint 42 viewed from the front. The cam follower 110 is pressed against the cylindrical cam surface 106a by the force of the spring 116. Therefore, the inclination of the cylindrical cam surface 106a converts the force of the spring 116 into a moment that rotates upward about the horizontal shaft 40. This makes it possible to reduce the downward rotational force of the rotation-side member 118 due to the weight of distal side from the horizontal shaft 40, as described above. This reduces the burden on the patient during surgery.

Generally, a spring having a linear characteristic in which displacement and load are proportional is used as the spring 116, but if the cam curve of the cam surface 106a is appropriately designed, the same effect can be obtained by a spring having characteristics such as constant load and non-linearity.

Next, a method of passing the cable in the present embodiment will be described.

In a drive device used in a robot, a cable is often passed through the joint, but in the present embodiment, since the self-weight compensating mechanism 100 is provided in the second passive joint 42, the inside of the horizontal shaft 40 is occupied by a mechanism component, and the cable or the like cannot be passed therethrough. Therefore, a routing method of the cable for reducing the load on the cable as much as possible in the configuration of the present embodiment will be described below.

Figure 4:
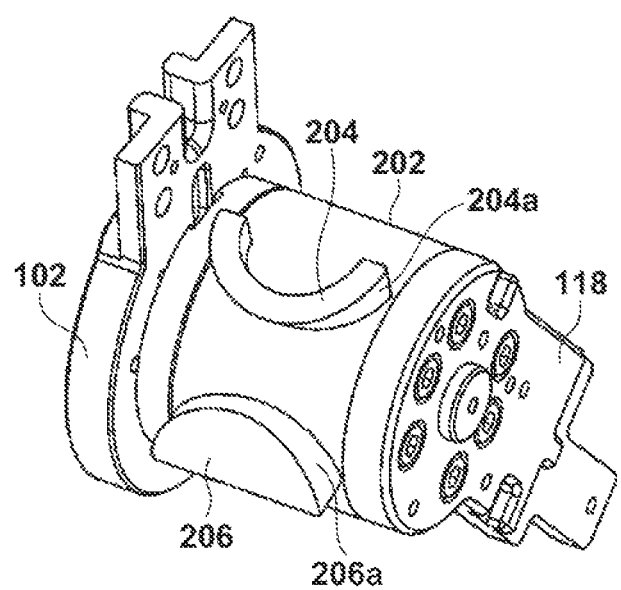
FIG. 4 is a view showing a state in which the cable guide member is attached to the second passive joint.

FIG. 4 is a view showing a state in which the cable guide member 202 is attached to the second passive joint 42 in the present embodiment.

Cable guide member 202 is a pipe-shaped member that can be freely rotated coaxially with the horizontal shaft 40 without affected by any of the horizontal shaft 40, the fixed-side member 102, and the rotation-side member 118 in FIG. 2. Further, on the outer peripheral surface of the cable guide member 202, as shown in FIG. 4, the guide portion A204 and the guide portion B206 having an arcuate portion are disposed. The cables slide over the arcuate surfaces 204a. 206a of the guide portions A204, B206. Here, in FIG. 4, the guide portion A204 and the guide portion B206 differ in shape. This is a contrivance for avoiding other components, and it is possible to perform the same function with any shape as long as it has at least a surface for guiding the cable.

FIGS. 5A-5D are diagrams showing an example of how cables are routed. Note that, the technique shown here is applicable not only to electrical cables, but is also applicable to cable-like members, such as a fluid tube or an optical fiber. The cable A210 and the cable B212 are disposed while bending three-dimensionally around the cable guide member 202, and relative movement occurs between the cable guide member 202.

Figure 5A:
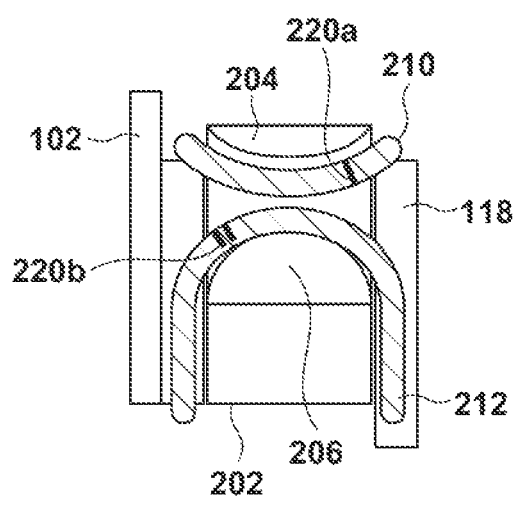
FIGS. 5A-5D are diagrams showing examples of how cables are routed.
Figure 5B:
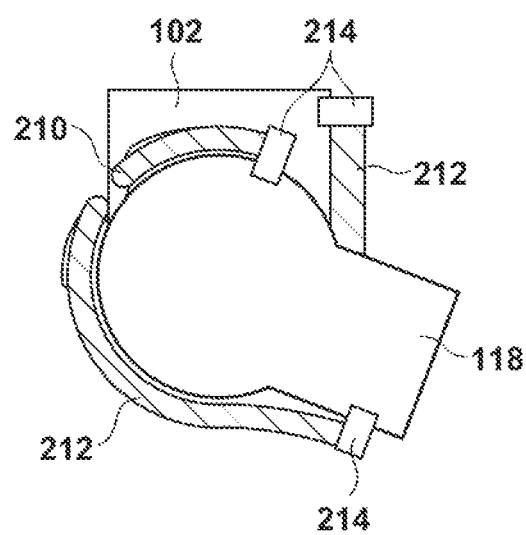

FIGS. 5A and 5B are diagrams showing the state of the cable A210, the cable B212 and the cable guide 202 when the horizontal shaft 40 is at an angle. There are two types of cable A210 and cable B212, but only one is a cable that is routed distally, and the other may be a mechanical wire.

One end and the other end of each cable are fixed by a cable fixing member 214 to the fixed-side member 102 and the rotation-side member 118, and enter the region of the cable guide member 202 so as to be wound around the shaft.

Note that, for convenience of illustration, although the cable fixing member 214 of the fixed-side member 102 is not drawn for the cable A210, it is fixed to the fixed-side member 102 similarly to the cable B212.

Here, consider the case where the rotational angle of the horizontal shaft 40 is changed so that the state of FIGS. 5A and 5B changes to the state of FIGS. 5A and 5B. There is no relative sliding with respect to the cable in both regions of fixed-side member 102 and the rotation-side member 118, and there is only a simple winding operation. On the other hand, in the region of the cable guide member 202, either cable slides relative to the cable guide member 202. As indicated by the positions of the marks 210a and 210b, the cable A210 and the cable B212 move in opposite directions, respectively. Further, at this time, the cable guide member 202, since it is pulled by the cable B212, rotates around the horizontal shaft 40, and the position when viewed from the fixed-side member 102 is changed.

Figure 5C:
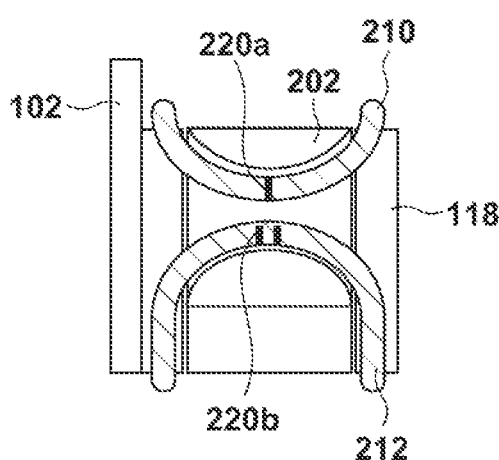
Figure 5D:
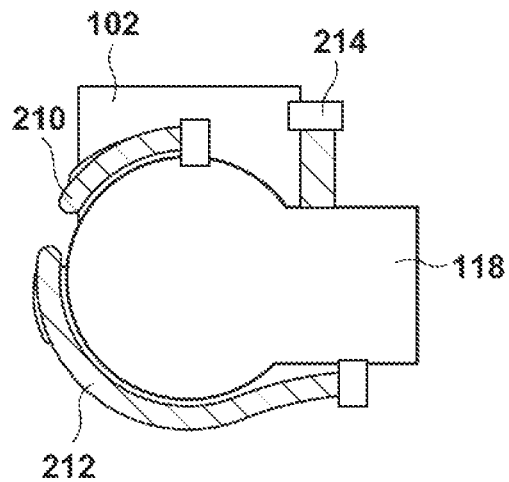

Next, consider the case where the rotational angle of the horizontal shaft 40 is changed so that the state of FIGS. 5C and 5D changes to the state of FIGS. 5A and 5B. At this time, since the cable A210 performs an operation to pull the cable guide member 202, the cable guide member 202 rotates in the opposite direction and returns to the state shown in FIGS. 5A and 5B. Since the cable for wiring is also used to drive the cable guide member 202, the cable can pass through the joint portion without changing the cable length while maintaining a reasonable radius of curvature with respect to the cable.

In the example shown here, by arranging the cable A210 and the cable B212 to face each other, the cable guide member 202 is driven in the opposite direction, but it is not limited to this method as long as a similar effect can be obtained. For example, a method of providing a torsion spring such as moment is always applied in a certain direction to the cable guide member, or a method of driving the cable guide member by a gear or the like interlocked with the angle of the horizontal shaft is also conceivable. In such a manner, either the cable A210 or the cable B212 path alone can behave in a similar manner.

Figure 6A:
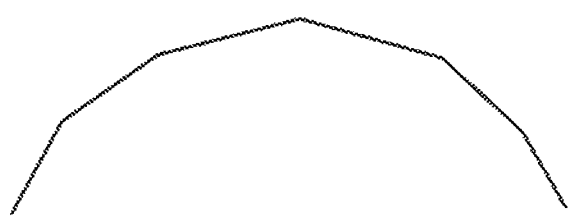
FIGS. 6A and 6B are diagrams showing a modification of the guide portion of the cable.
Figure 6B:
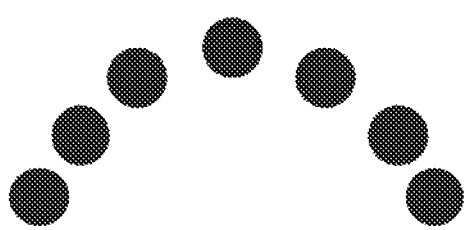

In the above explanation, the guide surfaces of the guide portion A204 and the guide portion B206 are described as arc-shaped, but the present invention is not limited to the arc-shaped shape. For example, the guide surface does not need to have a true circle shape even if arcuate, but the guide portion may have shape whose envelope has a shape close to the arc shape, such as polygonal shape close to arc shape as shown in FIG. 6A or the shape in which pins and balls are arrayed close to the arc shape as shown in FIG. 6B.

Next, a method of transmitting power to a portion ahead of the passive joint 42 will be described. In the section on the related art, it was described that when a passive joint is provided, since power cannot be transmitted to the distal side of the joint, it is necessary to attach an actuator to the distal side of the passive joint. However, in the case of a simple operation, it may be easier to mechanically transmit power without providing an actuator to the distal side of the passive joint. Here, the mechanism will be described.

Figure 7:
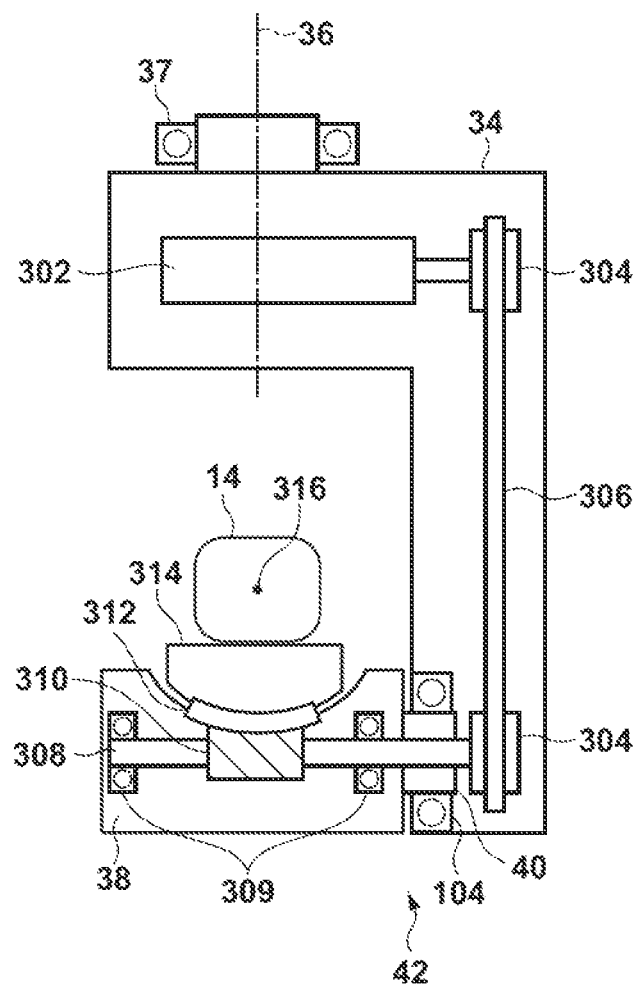
FIG. 7 is a diagram showing an example of a mechanism for transmitting power to a portion ahead of the passive joint.

FIG. 7 is a diagram showing an example of a mechanism for transmitting power to a portion ahead of the passive joint. Since the first passive joint 37 and the second passive joint 42 are passive joints having no actuator, the fixed-side member 34 can freely rotate about the vertical rotation axis 36, and the rotation-side member 38 can freely rotate about the horizontal shaft 40. In general, the horizontal shaft 40 and the vertical axis 36 intersect at one point orthogonally, but this is not necessary.

In FIG. 7, the rotational force of the rotation driving source 302 made of a motor or the like is transmitted to the worm shaft 308 through the pulley 304 and the belt 306. Here, the worm shaft 308 and the horizontal shaft 40 is coaxial, and each axis can be rotated independently. When the worm shaft 308 is supported and rotated by the worm bearing 309, power is transmitted through the worm gear 310 to the worm wheel 312. Thus, the rotation operation member 314 that is a driven body is rotated around the rotation axis 316 perpendicular to the paper surface. The surgical tool 14 is mounted on the rotation operation member 314.

Note that, in FIG. 7, the worm wheel 312 is not provided on entire circumference, but there are teeth only in a portion. If it is required to rotate one rotation of the rotation operation member 314, the worm wheel 312 is provided on the entire circumference. If there can be a limitation in the rotation angle, it may only be provided in a portion as shown in FIG. 7.

Here, the rotation operation member 314 must move while being restrained in a curved shape. An example of a structure enabling this is shown in FIG. 8.

Figure 8:
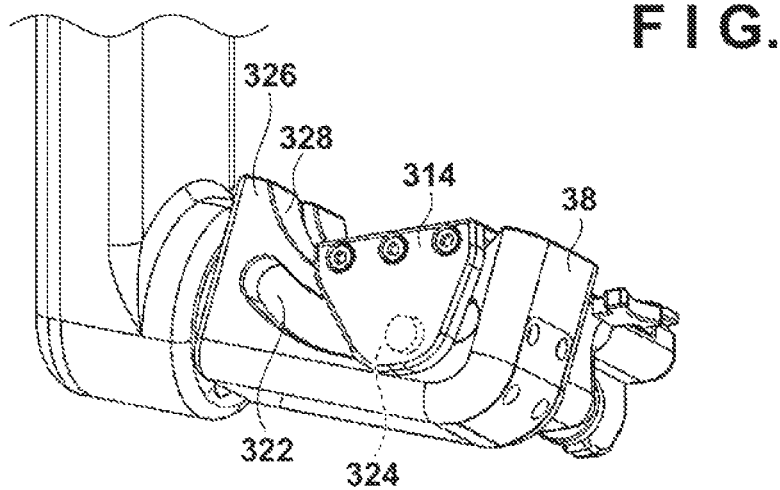
FIG. 8 is a diagram showing a structure for guiding the movement of the rotation-side member.

In FIG. 8, the rolling bearing 324 such as a bearing moves in the groove 322 formed in the rotation-side member 38, and the rotation operation member 314 can be moved while being restrained in a curved shape. However, since only the rolling bearing 324 cannot support movement in all directions, the rotation operation member 314 is slidably supported by the side surface 326 and the R guide surface (sliding surface) of the rotation-side member 328.

Returning to FIG. 7, the power generated by the rotation driving source 302 is transmitted to the worm wheel 312 through the pulley 304, the belt 306, and the worm gear 310, and the rotation operation member 314 is driven to rotate. At this time, if the worm wheel 312 is locked, or if the load is very large, the torque for rotating the worm shaft 308 becomes a torque for rotating the horizontal shaft 40. However, since the reduction ratio by the worm gear is generally very large, it is slight even if the torque to rotate the horizontal shaft is generated.

Generally, a surgical tool 14 in the shape of a long shaft such as a forceps or an endoscope is mounted on the rotation operation member 314, and is supported by the outer cannula 13. Therefore, even when a slight torque is generated in the horizontal shaft 40, the rotation operation member 314 is not rotated around the horizontal shaft 40. It can also be solved by adding a friction force generating mechanism (brake or damper) that does not affect the passive rotation of the horizontal shaft 40.

Figure 9:
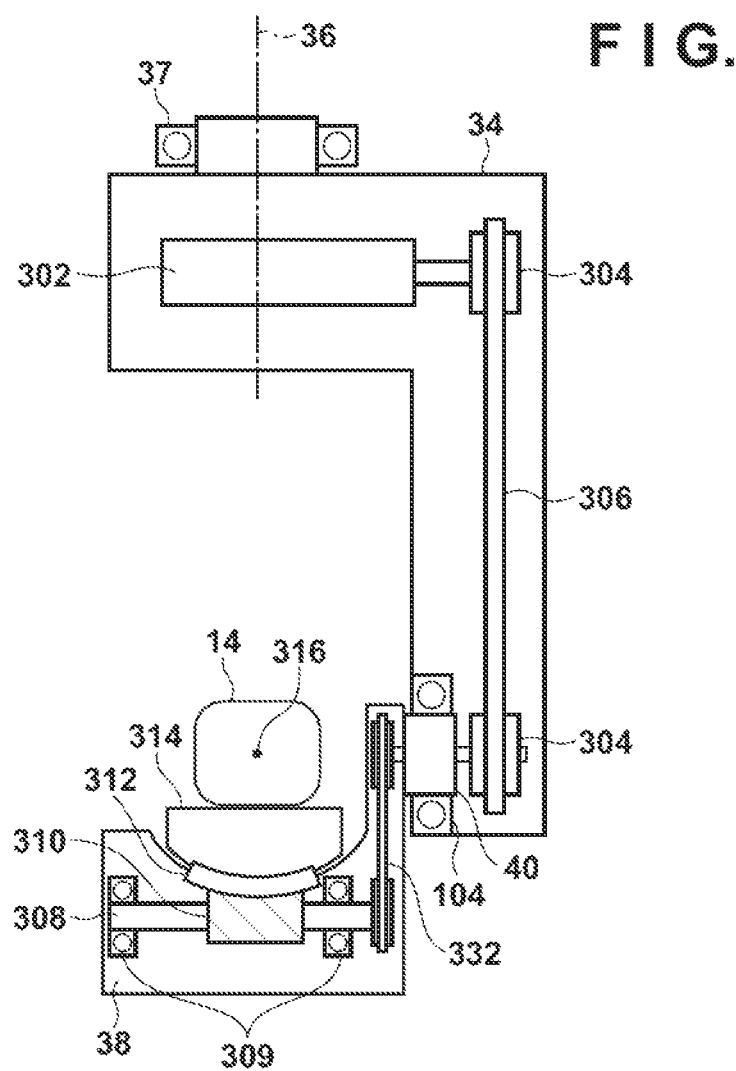
FIG. 9 is a diagram showing a power transmission mechanism obtained by offsetting the shaft.

In the mechanism shown in FIG. 7, although the horizontal shaft 40 and the rotation axis 316 of the rotation operation member 314 do not intersect, the vertical axis 36, the horizontal shaft 40 and the rotation axis 316 can intersect at one point as shown in FIG. 9 by offsetting the axis by the second belt 332.

Further, in the above example, it has been described that power is transmitted from the rotation driving source 302 by the belt 306, but it may be via a gear or similar transmission mechanism.

Next, a mechanism for attaching and detaching the surgical tool 14 to and from the rotation operation member 314 will be described.

Generally, surgical tools are attached to distal side of the passive joints and are frequently removed for replacement. Here, a mechanism that enables attachment and detachment of the surgical tool 14 to and from the rotation operation member 314 described above will be described.

Figure 10:
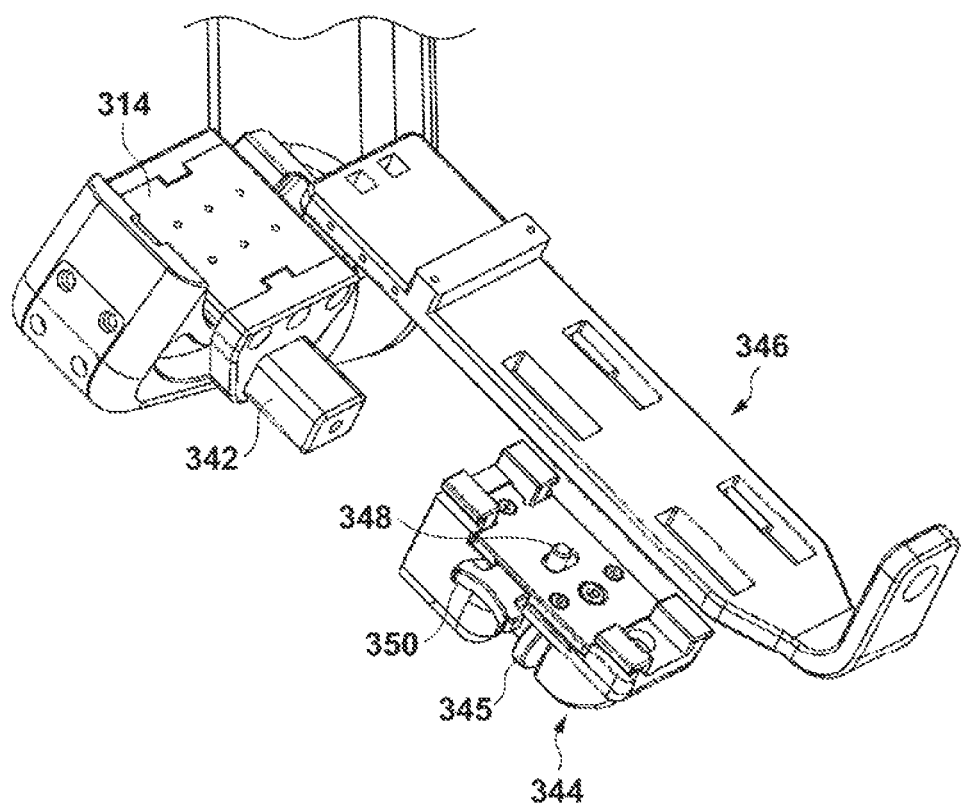
FIG. 10 is a diagram showing an example of the attachment/detachment mechanism of the surgical tool.

FIG. 10 is a view showing an example of the attachment/detachment mechanism of the surgical tool 14. As shown in FIG. 9, the rotation operation member 314 is provided with a fixing projection 342, and the fixing adapter 344 is attached so as to engage with the fixing projection 342. A fixing screw 345 or the like is used for the mounting, but the fixing method is not limited thereto.

A medical tool adapter 346 is detachably mounted to the fixing adapter 344. The medical tool adapter 346 is an adapter for attaching the surgical tool 14 to the fixing adapter 344, and may have several types according to the shape of the surgical tool 14 to be attached. A fixing claw 348 biased by a spring (not shown) is disposed on the fixing adaptor 344, and the medical tool adaptor 346 is engaged with the fixing claw 348 and attached to the fixing adaptor 344. The medical tool adapter 346 can also be removed from the fixing adapter 344 by pushing on the release lever 350.

Figure 11:
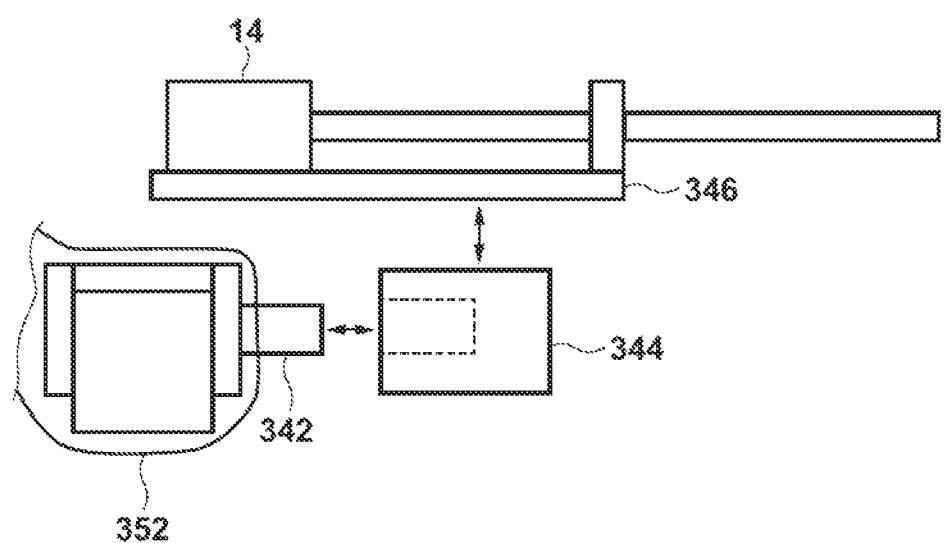
FIG. 11 is a diagram showing the arrangement of drapes.

Next. FIG. 11 is a diagram showing an arrangement of drapes. Generally, since a robot cannot be cleaned or sterilized, the robot is covered by a bag-like covering 352 called as a drape to separate a clean portion and a non-clean portion. In this embodiment, as shown in FIG. 11, a hole is provided in a part of the cover 352 to expose the fixing projection 342, and the fixing adapter 344 is attached.

Since the fixing projection 342 is a non-clean portion, it must be exposed as little as possible. In the structure of the present embodiment, since the medical tool adapter 346 can be removed without removing the fixing adapter 344, it is possible to attach and detach the device without touching the exposed non-clean portion.

As described above, according to the above embodiment, by providing the passive joint with the self-weight compensation mechanism by the spring, it is possible to reduce the downward rotational force applied to the rotation-side member by the weight of the tip side while suppressing the enlargement of the joint.

Further, by placing a pipe-shaped cable guide member having arcuate cable guide surface and being rotatable around the horizontal axis on the second passive joint, even when providing the self-weight compensation mechanism to the passive joint, it is possible to perform routing of the cable without putting a burden on the cable.

Further, by providing the power transmission mechanism as described above in the passive joint, it is possible to transmit power to a portion ahead of the passive joint with a simple configuration.

This application claims the benefit of Japanese Patent Application No. 2019-220499, filed Dec. 5, 2019, which is hereby incorporated by reference herein in its entirety.

What is claimed is:

1. A passive joint device for supporting a rotation-side member rotatably about a horizontal axis in a vertical direction with respect to a fixed-side member, comprising:
   a cylindrical cam member having a cylindrical surface centered on the horizontal axis and fixed to the fixed-side member, the cam member having a pair of cam surfaces symmetrically arranged on the cylindrical surface about the horizontal axis and formed obliquely along the horizontal axis;
   a pedestal slidably disposed along the horizontal axis within the horizontal axis fixed to the rotation-side member, the pedestal having a pair of cam followers that contact with each of the pair of cam surfaces; and
   a spring disposed inside the horizontal axis fixed to the rotation-side member, the spring biasing the pedestal toward the fixed-side member along the horizontal axis, wherein the spring force causes the pair of cam followers to come into contact with the pair of cam surfaces, push the pair of cam surfaces, and provide upward rotational force to the rotation-side member to reduce the downward rotational force of the rotation-side member by the weight applied to the rotation-side member.

2. The passive joint device according to claim 1, wherein the cam followers are rotatably disposed at opposite ends of the pedestal.

3. The passive joint device according to claim 1, wherein the pedestal is slidably supported with respect to the horizontal axis by a slide bearing rotatably disposed on the pedestal.

4. The passive joint device according to claim 1, wherein the cam surface is formed in a curved surface corresponding to the characteristics of the spring displacement and load.

5. The passive joint device according to claim 1, further comprising a guide member for guiding a pair of cables, one end of each of which is fixed to the fixed-side member and the other end of each of which is fixed to the rotation-side member,
wherein the guide member includes a pipe-shaped member which is rotatably disposed with respect to the horizontal axis, a pair of portions being formed to face each other on the outer surface of the guide member and slidably guide the pair of cables respectively, and wherein the guide member rotates about the horizontal axis while guiding the pair of cables as the pair of cables move in the same direction in accordance with relative rotation between the fixed-side member and the rotation-side member.

6. The passive joint device according to claim 1, further comprising a power transmission mechanism for transmitting power from the fixed-side member to the rotation-side member,
wherein the power transmission mechanism includes:
a rotation driving source disposed on the fixed-side member;
a rotation shaft coaxial with the horizontal axis to which a rotational force is transmitted from the rotation driving source;
a worm gear disposed on the rotation shaft;
a worm wheel engaging with the worm gear; and
a rotation operation member fixed to the worm wheel and rotating about an axis perpendicular to the horizontal axis.

7. The passive joint device according to claim 6, wherein the rotation-side member has an arc-shaped sliding surface for guiding rotation of the rotation operation member.

8. The passive joint device according to claim 1, further comprising a power transmission mechanism for transmitting power from the fixed-side member to the rotation-side member,
wherein the power transmission mechanism includes:
a rotation driving source disposed on the fixed-side member;
a first rotation shaft coaxial with the horizontal axis to which a rotational force is transmitted from the rotation driving source;
a second rotation shaft to which a rotational force is transmitted from the first rotation shaft;
a worm gear disposed on the second rotation shaft;
a worm wheel that engages with the worm gear; and
a rotation operation member that is fixed to the worm wheel and rotates about an axis perpendicular to the horizontal axis.

9. The passive joint device according to claim 8, wherein the second rotation shaft is offset from the horizontal axis such that the axis of rotation of the rotation operation member is orthogonal to the horizontal axis.

10. The passive joint device according to claim 8, wherein the rotation-side member has an arc-shaped sliding surface for guiding the rotation of the rotation operation member.

\* \* \* \* \*